US006320075B1

United States Patent
Ruedinger et al.

(10) Patent No.: US 6,320,075 B1
(45) Date of Patent: Nov. 20, 2001

(54) PROCESS AND APPARATUS FOR PREPARING SATURATED CARBOXYLIC ACIDS HAVING ONE TO FOUR CARBON ATOMS

(75) Inventors: Christoph Ruedinger, Starnberg; Hans-Juergen Eberle, München, both of (DE); Michael Hallmann, Ach (AT)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/520,454

(22) Filed: Mar. 8, 2000

(30) Foreign Application Priority Data

Mar. 11, 1999 (DE) .............................................. 199 10 866

(51) Int. Cl.$^7$ ................................................ C07C 51/215
(52) U.S. Cl. ...................... 562/549; 562/523; 562/512.2
(58) Field of Search ..................... 562/523, 549, 562/512.2

(56) References Cited

U.S. PATENT DOCUMENTS

| 3,431,297 | 3/1969 | Brockhaus . |
|---|---|---|
| 3,704,317 | 11/1972 | Yamashita et al. . |
| 3,917,682 | 11/1975 | Mizukami et al. . |
| 4,146,734 | 3/1979 | Slinkard . |
| 5,780,679 | * 7/1998 | Egly et al. . |
| 6,051,736 | * 4/2000 | Schraut et al. . |

FOREIGN PATENT DOCUMENTS

| 1 279 011 | 10/1968 | (DE) . |
|---|---|---|
| 1 921 503 | 11/1969 | (DE) . |
| 2 149 752 | 4/1972 | (DE) . |
| 196 49 426 | 6/1998 | (DE) . |
| 198 23 052 | 11/1999 | (DE) . |
| 19823052-A1 | * 11/1999 | (DE) . |
| 19823088-A1 | * 11/1999 | (DE) . |
| 198 23 088 | 11/1999 | (DE) . |
| 98/23371 | 6/1998 | (WO) . |

OTHER PUBLICATIONS

English Derwent Abstract AN 2000–014559 [02] corresp. to DE 198 23 052.
English Derwent Abstract AN 2000–001435 [01] corresp. to DE 198 23 088.
English Derwent Abstract AN 1972–24043T [15] corresp. to DE 2 149 752.
PEP Report No. 37A (1973).
R. P. Lowry, A. Aguilo, Hydrocarbon Processing, 10, (1974), 103.
English Derwent Abstract AN 1998–313425 [28] corresp. to DE 196 49 426.
Ullmanns Encyclopädie der technischen Chemie 4th edition, vol. 2, 1972, p. 575–576, corresp. to Fohann Schlauer, Manfred Vinebel, Absorption.

* cited by examiner

Primary Examiner—Paul J. Killos
Assistant Examiner—Robert W. Deemie
(74) Attorney, Agent, or Firm—Collard & Roe, P.C.

(57) ABSTRACT

A process and an apparatus are for preparing saturated carboxylic acids having from one to four carbon atoms by gas-phase oxidation at a reaction temperature of from 100° C. to 400° C. and pressures of from $1.2 \times 10^5$ to $51 \times 10^5$ Pa in the presence of saturated or unsaturated $C_4$-hydrocarbons and mixtures thereof. Also present in the reactor are an oxygen-containing gas and water vapor and in the presence of at least one catalyst, with part of the reactor outlet gas being recirculated in a reaction gas circuit. The acid concentration in the recirculated portion is reduced by means of a separation step, and the crude acid is separated from the reactor outlet gas by means of a countercurrent scrubber.

20 Claims, 2 Drawing Sheets

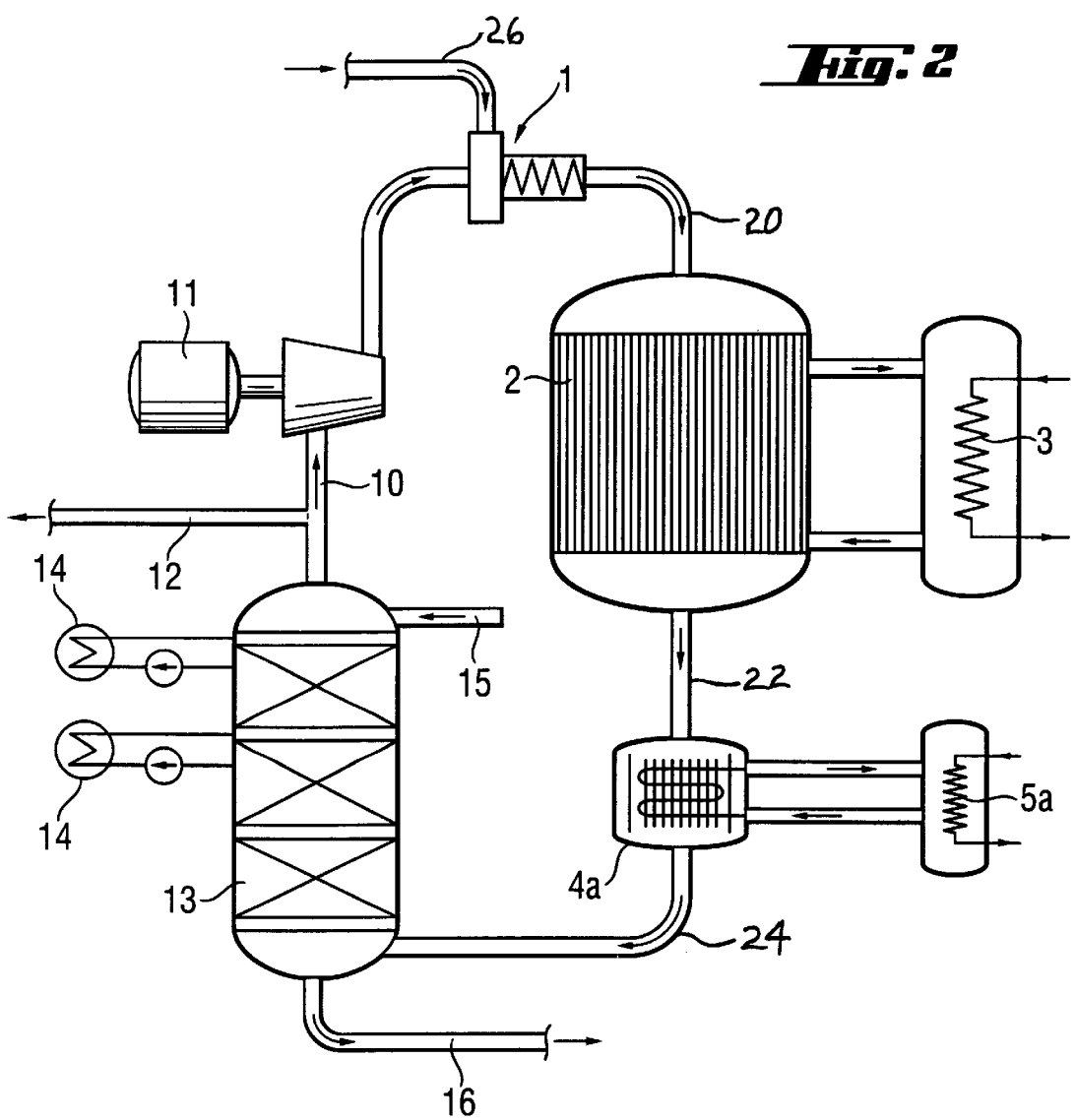

PROCESS AND APPARATUS FOR PREPARING SATURATED CARBOXYLIC ACIDS HAVING ONE TO FOUR CARBON ATOMS

BACKGROUND OF THE INVENTION

1. Field of the Invention

The present invention relates to a process for preparing saturated carboxylic acids having from one to four carbon atoms, and also an apparatus for carrying out the process.

2. The Prior Art

It is known that acetic acid can be prepared by gas-phase oxidation of $C_4$-hydrocarbons in the presence of a catalyst. Most descriptions provide for the reaction gas mixture to be passed once over the catalyst, for the acetic acid formed to be separated off by condensation and for the remaining gas to be discarded. For example, U.S. Pat. No. 3,917,682 describes a procedure in which acetic acid is obtained by butane and/or butene oxidation in the presence of a Ti/V catalyst having a high proportion of rutile. The acetic acid is isolated by partial. condensation of the reaction mixture. The remainder of the reaction gas is not recirculated. Such processes have to achieve a high butene conversion on only one pass through the reactor, which can be successfully achieved with small yields or low space-time outputs. For this reason, it has not yet been possible to find an economically satisfactory process on this basis.

U.S. Pat. No. 4,146,734 discloses that the gas-phase oxidation of butene to acetic acid can be carried out in the presence of a catalyst comprising lanthanide compounds. A method of isolating the acetic acid and further useful materials formed during the gas-phase oxidation is not disclosed.

DE-A 2,149,752 and DE-A 1,279,011 describe processes for the catalytic gas-phase oxidation of butene to acetic acid in the presence of specific catalysts. A disadvantage of this procedure is that in the indicated recirculation of the uncondensable proportion of the reaction gas, the formic acid obtained as a useful material decomposes. DE-A 1,921,503 refers to the possibility of recirculating the unreacted proportion of the reaction mixture to the reactor in the preparation of acetic acid by means of catalytic gas-phase oxidation of butene. However it is expressly stated that a circulating gas process is uneconomical.

A process was developed to the pilot scale by Chemische Werke Hüls and described in various publications (R. P. Lowry, A. Aguilo, *Hydrocarbon Processing*, 10, (1974), 103; PEP Report No. 37A (1973)). This provides for the direct, untreated recirculation of ⅘ of the gas mixture leaving the reactor. In this embodiment, part of the reaction product is circulated without removal of the acids and only part is separated off for isolating the acetic acid. In this process, there is considerable accumulation of organic acids in the reaction gas, as a result of which both acetic acid and formic acid are obtained in an unsatisfactory yield.

WQ-A 9,823,371 discloses a process for preparing acetic acid by gas-phase oxidation of unsaturated $C_4$-hydrocarbons using a coated catalyst comprising a support body and a catalytically active mixed oxide composition. These mixed oxides are selected from the group consisting of titanium dioxide, zirconium dioxide, tin dioxide, aluminum oxide and vanadium pentoxide applied to the outer surface of the support body. After the reaction, the acetic acid formed is separated off by cooling and precipitation or by absorption in a suitable solvent.

DE-A 19,823,052 describes a process for preparing acetic acid by gas-phase oxidation of saturated $C_4$-hydrocarbons and their mixtures with unsaturated $C_4$-hydrocarbons. This process uses a coated catalyst comprising an inert, nonporous support body and a catalytically active mixed oxide composition comprising titanium dioxide and vanadium pentoxide applied to the outer surface of the support body. In this process, a gas mixture comprising an oxygen-containing gas and $C_4$-hydrocarbons together with water vapor is reacted over the coated catalyst at a temperature of from 100° C. to 400° C. and a gauge pressure of from $1.2 \times 10^5$ to $51 \times 10^5$ Pa. No method of isolating the acetic acid and further useful materials formed during the gas-phase oxidation is indicated.

DE-A 19,823,088 describes a process for preparing saturated carboxylic acids having from 1 to 4 carbon atoms by gas-phase oxidation in the presence of saturated and/or unsaturated $C_4$-hydrocarbons, an oxygen-containing gas and water vapor and in the presence of at least one catalyst. In this process, part of the gas leaving the reactor is recirculated in a reaction gas circuit. This circuit is designed so that part of the organic acids formed in the gas-phase oxidation is removed from the gas leaving the reactor. However, only uneconomical methods such as partial condensation of the gas mixture or rectification processes, if desired with the addition of auxiliaries (e.g. extractive rectification), are indicated for separating off the crude acid.

SUMMARY OF THE INVENTION

It is therefore an object of the present invention to provide a process for preparing saturated carboxylic acids having from one to four carbon atoms, in particular acetic acid, by gas-phase oxidation of saturated and/or unsaturated $C_4$-hydrocarbons. This process provides high acid yields and in which the by-products are obtained as useful materials.

It has surprisingly been found that the preparation of saturated carboxylic acids having from one to four carbon atoms by gas-phase oxidation of saturated and/or unsaturated $C_4$-hydrocarbons can be carried out in particularly high yields. This result occurs if a substream of the reactor outlet gas mixture which has been largely freed of acids by means of an aqueous countercurrent scrub is recirculated to the reactor inlet.

The invention provides a process for preparing saturated carboxylic acids having from one to four carbon atoms by gasphase oxidation at a reaction temperature of from 100° C. to 400° C. and pressures of from $1.2 \times 10^5$ to $51 \times 10^5$ Pa by the reaction of saturated or unsaturated $C_4$-hydrocarbons and mixtures thereof, an oxygen-containing gas and water vapor in the presence of at least one catalyst. Also part of the reactor outlet gas is recirculated in a reaction gas circuit and the acid concentration in the recirculated portion is reduced by means of a separation step, wherein the crude acid is separated from the reactor outlet gas by means of a countercurrent scrub.

In the process of the invention, the reaction gas circuit is designed so that part of the organic acids, primarily acetic acid and formic acid, are removed from the reactor outlet gas. This removal is by either the gas mixture leaving the reactor or by the recirculated gas mixture, by means of a countercurrent scrub with a suitable solvent, preferably water. This separation is designed so that the partial pressure of these acids at the reactor inlet remains low. Also unreacted $C_4$-hydrocarbons and intermediates which can be reacted further to give acetic acid, for example include acetaldehyde, acetone, methyl ethyl ketone and 2-butanol. These compounds mostly remain in the circulation gas and are recirculated to the reactor inlet.

Solvents used for the countercurrent scrub are preferably compounds selected from the group consisting of diphenyl oxide, biphenyl, aromatic and aliphatic ketones and ethers, phthalic acid and phthalic acid derivatives, phthalide, aliphatic dicarboxylic acids, adipic acid and adipic acid derivatives, maleic acid and maleic acid derivatives, carboxyacetic acids, benzoic acid and benzoic acid derivatives, lactones, propylene carbonate, dialkyl carbonates, trialkyl phosphates, trialkylamines sulfolane and sulfolane derivatives, alkylpyrrolidones, low molecular weight compounds, for example, liquids, polymers or oligomers, polyvinylates, polyacrylates, polyethers, polyketones, water and mixtures of such compounds. The particularly preferred solvent is water.

A suitable preferred solvent has to have the following properties: good selectivity with respect to the water/acid separation; high affinity for organic acids (high partition coefficient) in order to keep the amount of absorption medium required low; low volatility under the absorption conditions in order to keep losses into the circulating gas low; and the amounts of absorption medium going into the circulating gas must not have an adverse effect on the catalytic oxidation reaction. The solvent melting point has to be significantly below the absorption temperature. The solvent must not undergo any chemical reactions under the absorption/desorption conditions and regeneration conditions.

In one embodiment of the invention, the scrub of the reaction gas in the countercurrent absorption employed is advantageously designed so that the reaction gas flows through one or more apparatuses. This apparatus is selected from the group consisting of trickle towers and spray towers, absorbers having moving internal fittings, for example a rotation absorber, absorption towers containing random packing elements, absorbers containing internal fittings in the form of separation trays, for example bubble cap trays, valve trays, sieve trays, mesh trays or combinations thereof, and absorbers containing ordered packing, and water flows in countercurrent thereto through the absorber. The water vapor content of the gas stream leaving the absorber is determined by the temperature prevailing at the absorber outlet and the operating pressure. The temperature is determined by the amount of heat removed from the absorber and the amount and temperature of the scrubbing water stream and is generally from 50° C. to 200° C. The remaining acid content in the gas stream leaving the absorber is determined by pressure and temperature, the number of theoretical separation stages in the absorber and the amount of absorption medium fed in (water feed). In general, the process is carried out so that the countercurrent scrub reduces the residual acid concentration in the gas stream returned to the reactor to from 0.01 to 6% by volume.

Apart from acetic acid and formic acid, further useful materials obtained are propionic acid, maleic acid/maleic anhydride and acrylic acid. Part of the water obtained in the concentration and purification of the crude acid is, if desired after a chemical and/or physical treatment, fed back into the countercurrent absorption. Thus there is virtually no wastewater obtained in the overall process.

The crude acid which has been separated off is dried and purified by one or more suitable customary methods selected from the group consisting of liquid-liquid extraction, extractive rectification, azeotropic rectification, rectification and membrane separation processes. The low boiler compounds obtained in the concentration and purification of the crude acid can be recirculated to the countercurrent scrub. The low boiler compounds separated off prior to a further fractionation of the crude acid into its pure constituents can likewise, all or in part, be recirculated to the countercurrent scrub either alone or together with low boiler compounds from the purification and concentration.

The process of the invention is eminently suitable for the preparation of acetic acid and formic acid, particularly preferably for the preparation of acetic acid. A significant advantage of the process of the invention is that the by-products formed in the preparation of acetic acid are obtained as useful materials, especially in the form of formic acid.

The separation of the organic acids from the reaction mixture by countercurrent absorption according to the invention, for example by means of water, has a number of advantages over condensation. Firstly, this achieves a higher selectivity; secondly, the energy input required is reduced. Furthermore, there is a higher passive safety with respect to the explosion risk and the overall process can thereby be made simpler.

The saturated or unsaturated hydrocarbons having four carbon atoms which are used in the process of the invention are compounds selected from the group consisting of n-butane, i-butane, 1-butene, cis-2-butene, trans-2-butene, isobutene and 1,3-butadiene. Preference is given to n-butane and the butene isomers 1-butene, trans-2-butene and cis-2-butene and also mixtures containing high proportions of these compounds. In the process of the invention, the $C_4$-hydrocarbon fraction may further comprise linear and/or branched and/or cyclic hydrocarbons having more or less than four carbon atoms, for example methane, ethane, ethene, propene, propane, pentanes, pentenes, pentadienes, cyclopentane, cyclopentene, cyclopentadiene or methylcyclopentane. Likewise, alcohols, aldehydes, ethers, ketones and esters having from 1 to 8 carbon atoms may be present. Preference is given to cheap raw material mixtures from the petrochemicals industry, as starting materials. For example there is the "$C_4$ fraction" (predominantly butadiene and i-butene), "raffinate 1" (predominantly i-butene and n-butenes) and "raffinate 2" (predominantly butanes, 1-butene and 2-butenes), as starting material, or mixtures comprising such hydrocarbons. These can, if desired, be used after a pretreatment. such as a purification or hydrogenation.

The reaction temperature of the gas-phase oxidation is generally from 100° C. to 400° C., preferably from 150° C. to 250° C., particularly preferably from 180° C. to 230° C. The reaction is generally carried out at pressures of from $1.2 \times 10^5$ to $51 \times 10^5$ Pa, preferably from $4 \times 10^5$ to $41 \times 10^5$ Pa, particularly preferably from $9 \times 10^5$ to $17 \times 10^5$ Pa.

As oxygen-containing gas, it is possible to use air, air enriched with oxygen and preferably pure oxygen. However, an inert gas such as nitrogen can also be present in the process of the invention.

The proportion by volume of water vapor in the reactor inlet gas fed to the reactor is generally from 5 to 80% by volume, preferably from 5 to 40% by volume, particularly preferably from 5 to 30% by volume.

The proportion of butene in the reaction gas, measured at the reactor inlet, which can be present as starting material either alone or in admixture with further $C_4$-hydrocarbons, is from 1 to 10% by volume, preferably from 1.5 to 3.5% by volume. The proportion of butane in the reaction gas, measured at the reactor inlet, which can likewise be present as starting material either alone or in admixture with further $C_4$-hydrocarbons, is from 5 to 80% by volume, preferably from 5 to 60% by volume, particularly preferably from 10 to 50% by volume. The oxygen content of the gas stream fed to the reactor is from 1 to 35% by volume, preferably from 2 to 20% by volume, particularly preferably from 3 to 12% by volume.

If desired, an inert gas can be present in the feed in a proportion of from 0 to 25% by volume. The proportion of carbon oxides and further reaction by-products in the reactor inlet gas depends on the reaction procedure and the separation of acid and is generally from 10 to 80% by volume, preferably from 15 to 65% by volume. The proportions in % by volume of the individual constituents of the reactor inlet gas in each case add up to 100% by volume.

The mass of flow of gas which is recirculated is generally from 1 to 100 times the mass of flow of fresh starting material fed in. It is preferably from 5 times to 80 times, and is particularly preferably from 10 to 40 times.

Suitable catalysts for the process of the invention are all catalysts which have been described for the partial oxidation of saturated and/or unsaturated $C_4$-hydrocarbons to produce acetic acid. Preference is given to mixed oxide catalysts which comprise vanadium oxides. Particular preference is given to coated catalysts which are described in DE-A 19,649,426. DE-A 19,649,426, whose disclosure in this respect is to be regarded as part of the present application and is herewith incorporated by reference. The catalyst described therein is a coated catalyst comprising an inert nonporous support body and a catalytically active mixed oxide composition applied to the outer surface of the support body. The catalytically active mixed oxide composition comprises a) one or more oxides selected from the group consisting of titanium dioxide, zirconium dioxide, tin dioxide and aluminum oxide and b) from 0.1 to 1.5% by weight, based on the weight of component a) and per $m^2/g$ of specific surface area of component a), of vanadium pentoxide.

As additional components a), it is possible for one or more oxides selected from the group consisting of those of boron, silicon, hafnium, niobium, tungsten, lanthanum and cerium to be present. When the component a) is doped with the abovementioned oxides, the latter are generally present in an amount of from 1 to 30% by weight, based on the total weight of the component a).

In component b), part of the vanadium pentoxide, preferably from 10 to 90% by weight, may, if desired, be replaced by one or more oxides of molybdenum, chromium and antimony. If desired, one or more oxides of alkali metals, elements of main groups V and VI of the Periodic Table of the Elements and the transition metals may be present as additional components b). In general, the amount of these dopants is from 0.005 to 15% by weight, calculated as oxides and based on the total weight of the component b).

Preference is given to compositions having a high surface area of the component a) of from 40 to 300 $m^2/g$, with tin oxide, niobium oxide or tungsten oxide also being able to be present if desired, and containing a component b) which is doped with Mo and/or Cr and/or Sb and/or Au.

The catalytically active mixed oxide composition may, if desired, further comprise from 10 to 50% by weight, based on the total weight of the catalytically active mixed oxide composition, of inert diluents selected from the group consisting of silicon dioxide, silicon carbide and graphite.

The catalytically active mixed oxide composition is applied in a proportion of from 1 to 40% by weight, preferably from 5 to 25% by weight, in each case based on the total weight of the support body and active composition, as a coating to the outer surface of the support body. The layer thickness is generally from 10 to 2000 μm, preferably from 100 to 1000 μm. The coated catalyst can also comprise a plurality of layers which differ in their composition. It is also possible for one or more constituents of the active components a) and b) to be present in different concentrations in the individual layers.

Materials which are suitable for the inert, nonporous support body are all nonporous materials which are inert under the operating conditions of the gas-phase oxidation and are stable over the time of operation. Examples are steatite, Duranit, silicon carbide, magnesium oxide, silicon oxide, silicates, aluminates, metals such as stainless steel and also, if desired, mixtures of these materials. Preference is given to a ceramic material, for example steatite. The shape of the inert, nonporous support body can be any shape desired. Examples of suitable shapes are spheres, cylinders, cuboids, tori, saddles, spindles and helices. The base bodies can also have one or more recesses such as depressions, grooves or holes, or projecting parts such as pegs, points or webs. Further examples are rings, ring segments, web rings, spheres with holes and sphere segments. Other suitable supports are ordered packings such as monoliths or cross-channel structures. Preference is given to support shapes having as high as possible a geometric surface area per volume, for example rings.

The dimensions of the support bodies are determined by the reactors for the gas-phase oxidation. In general, the shaped bodies have a length or diameter of from 2 to 20 mm. The wall thickness, for example in the case of rings or hollow cylinders, is advantageously from 0.1 to 4 mm.

As a reactor, it is possible to use designs which are suitable for carrying out oxidation reactions in the gas phase and are able to remove the high heat of reaction without excessive heating of the reaction mixture. The process of the invention can be carried out continuously or intermittently, i.e. the reactor inlet mixture can be fed in as a constant feed or with a cyclically varying feed composition. The gas mixture can react over the catalyst in a fixed bed, for example in a multitube reactor or tray reactor, or in a moving or fluidized bed. Preference is given to the cooled multitube reactors containing a fixed catalyst bed. Particular preference is given to configurations in which individual tubes having an internal diameter of from 10 mm to 50 mm and a length of from 1 m to 6 m are arranged in a bundle.

The flow rate, based on the empty tube, in the reaction tubes is generally from 0.1 m/s to 10 m/s, preferably from 0.3 m/s to 5 m/s, particularly preferably from 0.5 to 3 m/s.

The reaction tubes can be filled with catalyst of differing composition, shape and dimensions. The charge can be installed ill the reaction tubes so as to be homogeneous or have zonewise variation in the axial direction. Each zone may contain a randomly diluted or mixed catalyst.

The invention further provides an apparatus for preparing saturated carboxylic acids having from one to four carbon atoms by the process of the invention.

BRIEF DESCRIPTION OF THE DRAWINGS

Other objects and features of the present invention will become apparent from the following detailed description considered in connection with the accompanying drawings which disclose several embodiment of the present invention. It should be understood, however, that the drawings are designed for the purpose of illustration only and not as a definition of the limits of the invention.

In the drawings, wherein the same reference characters denote the same features throughout the several views:

FIG. 2 shows an apparatus for preparing acids by gas-phase oxidation of saturated and/or unsaturated hydrocarbons over a catalyst with circulation of part of the reaction gas downstream according to the process of the invention.

DETAILED DESCRIPTION OF PREFERRED EMBODIMENTS

Figure 1:
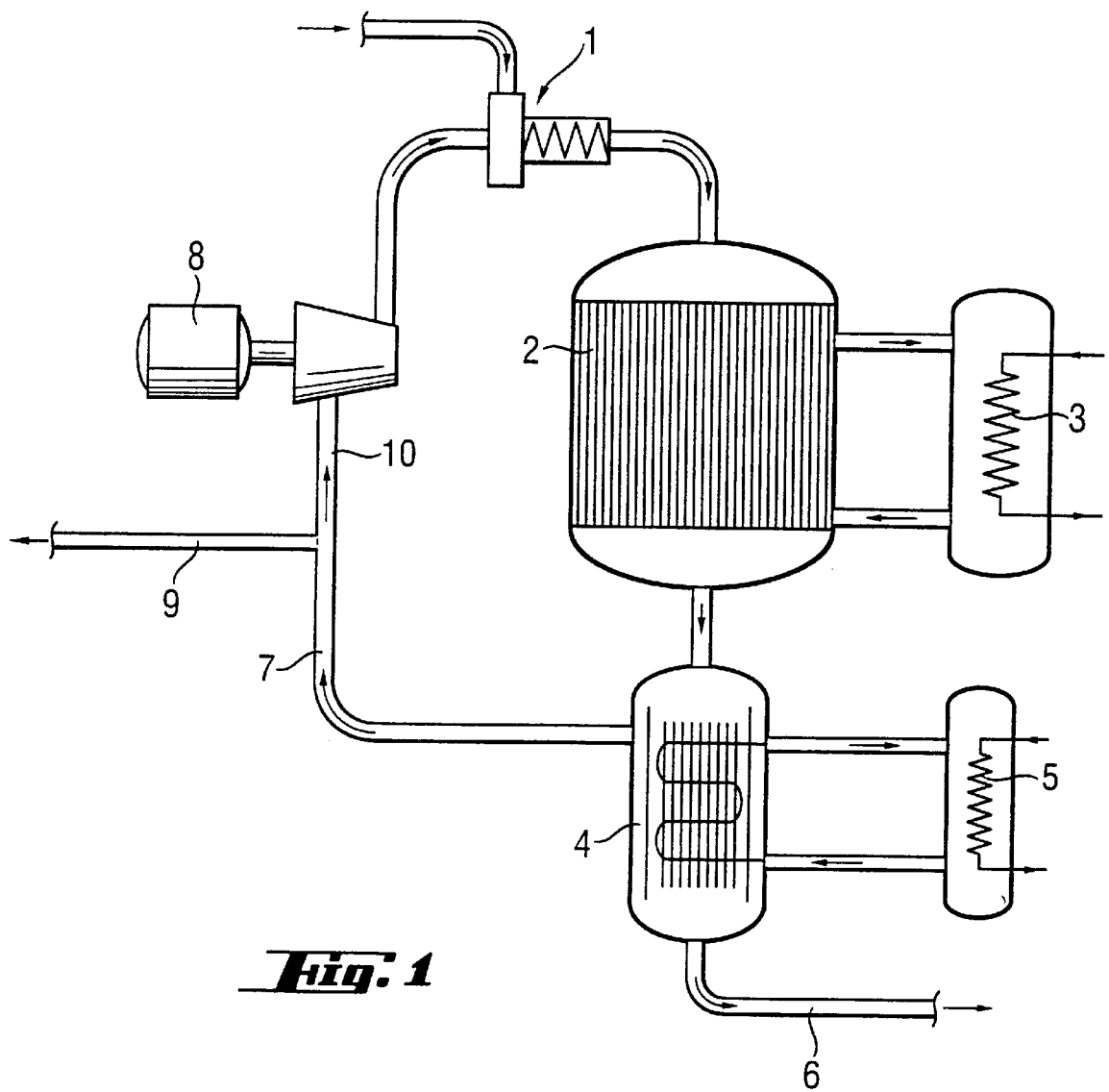
FIG. 1 shows an apparatus for preparing acids by gas-phase oxidation of saturated and/or unsaturated hydrocarbons over a catalyst with circulation of part of the reaction gas.

Turning now in detail to the drawings, FIG. 1 shows an apparatus for preparing acids by gas-phase oxidation of saturated and/or unsaturated hydrocarbons over a catalyst with circulation of part of the reaction gas. The acid is separated off from the main stream by cooling and/or condensation. Here, an oxygen-containing gas, oxygen or air or a mixture thereof, steam and the saturated and/or unsaturated hydrocarbons are fed in and mixed via a mixing zone 1 and fed to a multitube reactor 2 which is cooled by means of a cooling circuit 3. The main stream of the gas mixture leaving the reactor is passed through a product condenser 4 which is cooled by a cooling circuit 5. In this product condenser, the crude acid is separated off and passed via a line 6 to further work-up. The remaining reaction gas is recirculated via a line 7 to the mixing zone by means of a circulation gas compressor 8. A small waste gas stream is bled off via a line 9 to maintain steady-state conditions in the reaction circuit. The waste gas comprises predominantly carbon oxides and unreacted hydrocarbons and can be passed to thermal utilization (waste gas combustion) or other waste gas treatment. Most or only some of the hydrocarbons can be separated from this waste gas stream, for example by compression and/or cooling, and be returned as additional feed to the reaction circuit.

FIG. 2 shows an apparatus for preparing acids by gas-phase oxidation of saturated and/or unsaturated hydrocarbons over a catalyst with circulation of part of the reaction gas downstream according to the process of the invention. Here, the crude acid is separated off by means of a countercurrent absorption using a suitable solvent, for example water. In this embodiment, an oxygen-containing gas, oxygen or air or a mixture thereof and the saturated and/or unsaturated hydrocarbons are mixed with the recirculated gas stream via a mixer 1 and fed, together with the recirculated gas stream, to the multitube reactor 2 through conduit 20. Reactor 2 is cooled by means of a cooling circuit 3. The main stream of the gas mixture leaving the reactor is passed through conduit 22 to and through a gas cooler 4a which is cooled by a cooling circuit 5a. Downstream thereof, the reaction gas is passed through conduit 24 into an absorption column 13 which is equipped with one or more column coolers 14. In the uppermost column tray, a suitable solvent, for example water, is fed in through a pipe 15. In this absorption column, the crude acid is separated off by countercurrent scrubbing and is passed via a pipe 16 to further work-up. The remaining reaction gas is recirculated via a pipe 10 to the mixing zone by means of a circulation gas compressor 11. A small waste gas stream is bled off via a line 12 to maintain steady-state conditions in the reaction circuit.

The waste gas stream taken off comprises predominantly carbon oxides and unreacted hydrocarbons and can be passed to thermal utilization, for example waste gas combustion, to utilization as a material or to another waste gas treatment. Most or only part of the hydrocarbons in this waste gas stream can be liquefied by suitable methods, for example by compression or cooling or a combination of these methods. They are then separated from the uncondensable constituents and are returned through conduit 26 as additional feed to the reaction circuit, for example at the reactor inlet.

EXAMPLES

The following examples illustrate the invention. The selectivity [in mol %] was calculated as follows:

Acetic acid selectivity based on total $C_4$ conversion (mol %)=(((mol/h of acetic acid in the crude acid)/2)/(mol/h of butene reacted+mol/h of butane reacted))×100

Formic acid selectivity based on total $C_4$ conversion (mol %)=(((mol/h of formic acid in the crude acid)/4)/(mol/h of butene reacted+mol/h of butane reacted))×100

Catalysts Used in the Examples:

Catalyst A: The catalyst was produced by a method analogous to that described in DE-A-19,649,426. The active composition comprises oxides of titanium, vanadium and antimony of the empirical formula $Ti_aV_bSb_dO_e$ (a: 125; b: 10; d: 12; e: 293) and is applied in an amount of 9% by weight plus 1% by weight of graphite, based on the weight of the support, to steatite rings having the dimensions 7 mm external diameter×4 mm internal diameter×7 mm height.

Catalyst B: The catalyst was produced by a method analogous to that described in DE-A-19,649,426. The active composition comprises oxides of titanium, vanadium and antimony of the empirical formula $Ti_aV_bSb_dO_e$ (a: 125; b: 10; d: 12; e: 293) and is applied in a proportion of 10.8% by weight plus 1.2% by weight of graphite, based on the weight of the support, to steatite rings having the dimensions 7 mm external diameter×4 mm internal diameter×7 mm height.

Catalyst C: The catalyst was produced by a method analogous to that described in DE-A-19,649,426. The active composition comprises oxides of titanium, vanadium, molybdenum and antimony of the empirical formula $Ti_aV_bMo_cSb_dO_e$ (a: 122; b: 9; c: 5; d: 4; e: 288) and is applied in a proportion of 14.4% by weight plus 1.6% by weight of graphite, based on the weight of the support, to steatite rings having the dimensions 7 mm external diameter×4 mm internal diameter×4 mm height.

Catalyst D: The catalyst was produced by a method analogous to that described in DE-A-19,649,426. The active composition comprises oxides of titanium, vanadium and antimony of the empirical formula $Ti_aV_bSb_dO_e$ (a: 125; b: 10; d: 12; e: 293) and is applied in a proportion of 9.5% by weight plus 0.5% by weight of graphite, based on the weight of the support, to steatite rings having the dimensions 7 mm external diameter×4 mm internal diameter×7 mm height.

Catalyst E: The catalyst was produced by a method analogous to that described in DE-A-19,649,426. The active composition comprises oxides of titanium, vanadium and antimony of the empirical formula $Ti_aV_bSb_dO_e$ (a: 125; b: 10; d: 12; e: 293) and is applied in a proportion of 16.2% by weight plus 1.8% by weight of graphite, based on the weight of the support, to steatite rings having the dimensions 7 mm external diameter×4 mm internal diameter×7 mm height.

Comparative Example 1

(Circulation Process with Separation of Acid as Shown in FIG. 1):

A catalyst of type A was introduced to a fill height of 6000 mm into a reactor having a reaction tube internal diameter of 25 mm. As reaction gas, 1000 g/h of steam, 350 g/h of oxygen, 150 g/h of 1-butene and 200 g/h of n-butane were fed in. The flow of circulating gas was set so that 11,000 g/h of circulating gas flowed through the reactor in the steady state. The reactor was operated at a pressure of $11 \times 10^5$ Pa and a coolant temperature of 193° C.

The acid was separated from the reaction gas by partial condensation at 70° C.

Under these conditions, a butene conversion of 96% and a butane conversion of 22% were achieved. The acetic acid selectivity based on the total $C_4$ conversion was 61 mol % and the formic acid selectivity based on the total $C_4$, conversion was 12 mol %. The crude acid concentration was 21% by weight.

Example 1

(Circulation Process with Separation of Acid as Shown in FIG. 2):

A catalyst of type A was introduced to a fill height of 6000 mm into a reactor having a reaction tube internal diameter of 25 mm. As reaction gas, 345 g/h of oxygen, 144 g/h of 1-butene and 61 g/h of n-butane were fed in. The flow of circulating gas was set so that 10,000 g/h of circulating gas flowed through the reactor in the steady state. The reactor was operated at a pressure of $11 \times 10^5$ Pa and a coolant temperature of 190° C. The acid was separated from the reaction gas by absorption using 600 g/h of water (introduction at the top) in an absorber containing structured packing and. having an internal diameter of 43 mm and a packing height of 3240 mm at a temperature at the top of the absorber of 130° C.

Under these conditions, a butene conversion of 99% and a butane conversion of 65% were achieved. The acetic acid selectivity based on the total $C_4$ conversion was 63 mol % and the formic acid selectivity based on the total $C_4$ conversion was 13 mol %. The crude acid concentration was 31% by weight.

Example 2

(Circulation Process with Separation of Acid as Shown in FIG. 2):

A catalyst bed (upper zone) having a fill height of 3000 mm of catalyst B and a further catalyst bed (lower zone) having a fill height of 3000 mm of catalyst C. were introduced into a reactor having a reaction tube internal diameter of 25 mm. As reaction gas, 345 g/h of oxygen, 148 g/h of 1-butene and 60 g/h of n-butane were fed in. The flow of circulating gas was set so that 10,000 g/h of circulating gas flowed through the reactor in the steady state. The reactor was operated at a pressure of $11 \times 10^5$ Pa and a coolant temperature of 190° C.

The acid was separated from the reaction gas by absorption using 1000 g/h of water (introduction at the top) in an absorber containing structured packing and having an internal diameter of 43 mm and a packing height of 3240 mm at a temperature at the top of the absorber of 130° C.

Under these conditions, a butene conversion of 99% and a butane conversion of 66% were achieved. The acetic acid selectivity based on the total $C_4$ conversion was 64 mol % and the formic acid selectivity based on the total $C_4$ conversion was 13 mol %. The crude acid concentration was 23% by weight.

Example 3

(Circulation Process with Separation of Acid as Shown in FIG. 2):

A catalyst bed (upper zone) having a fill height of 3000 mm of catalyst B and a further catalyst bed (lower zone) having a fill height of 3000 mm of catalyst C. were introduced into a reactor having a reaction tube internal diameter of 25 mm. As reaction gas, 345 g/h of oxygen, 148 g/h of 1-butene and 60 g/h of n-butane were fed in. The flow of circulating gas was set so that 10,000 g/h of circulating gas flowed through the reactor in the steady state. The reactor was operated at a pressure of $11 \times 10^5$ Pa and a coolant temperature of 188° C.

The acid was separated from the reaction gas by absorption using 2000 g/h of water (introduction at the top) in an absorber (structured packing) having an internal diameter of 43 mm and a packing height of 3240 mm at a temperature at the top of the absorber of 130° C.

Under these conditions, a butene conversion of 99% and a butane conversion of 63% were achieved. The acetic acid selectivity based on the total $C_4$ conversion was 64 mol % and the formic acid selectivity based on the total $C_4$ conversion was 13 mol %. The crude acid concentration was 13% by weight.

Example 4

(Circulation Process with Separation of Acid as Shown in FIG. 2):

A catalyst bed (upper zone) having a fill height of 3000 mm of catalyst D and a further catalyst bed (lower zone) having a fill height of 3000 mm of catalyst E were introduced into a reactor having a reaction tube internal diameter of 25 mm. As reaction gas, 322 g/h of oxygen, 126 g/h of 1-butene and 48 g/h of n-butane were fed in. The flow of circulating gas was set so that 14,000 g/h of circulating gas flowed through the reactor in the steady state. The reactor was operated at a pressure of $13 \times 10^5$ Pa and a coolant temperature of 193° C.

The acid was separated from the reaction gas by absorption using 1000 g/h of water (introduction at the top) in an absorber (structured packing) having an internal diameter of 43 mm and a packing height of 3240 mm at a temperature at the top of the absorber of 130° C.

Under these conditions, a butene conversion of 99% and a butane conversion of 78% were achieved. The acetic acid selectivity based on the total $C_4$ conversion was 63 mol % and the formic acid selectivity based on the total $C_4$ conversion was 13 mol %. The crude acid concentration was 21% by weight.

Example 5

(Circulation Process with Separation of Acid as Shown in FIG. 2):

A catalyst bed (upper zone) having a fill height of 3000 mm of catalyst D and a further catalyst bed (lower zone) having a fill height of 3000 mm of catalyst E were introduced into a reactor having a reaction tube internal diameter of 25 mm. As reaction gas, 319 g/h of oxygen, 126 g/h of 1-butene and 48 g/h of n-butane were fed in. The flow of circulating gas was set so that 16,000 g/h of circulating gas flowed through the reactor in the steady state. The reactor was operated at a pressure of $15 \times 10^5$ Pa and a coolant temperature of 190° C.

The acid was separated from the reaction gas by absorption using 2000 g/h of water (introduction at the top) in an absorber (structured packing) having an internal diameter of 43 mm and a packing height of 3240 mm at a temperature at the top of the absorber of 130° C.

Under these conditions, a butene conversion of 99% and a butane conversion of 78% were achieved. The acetic acid selectivity based on the total $C_4$ conversion was 63 mol % and the formic acid selectivity based on the total $C_4$ conversion was 13 mol %. The crude acid concentration was 11% by weight.

While a few embodiments of the present invention have been shown and described, it is to be understood that many changes and modifications may be made thereunto without departing from the spirit and scope of the invention as define in the appended claims.

What is claimed is:

1. A process for preparing saturated carboxylic acids having from one to four carbon atoms comprising gas-phase oxidizing in a reactor at a reaction temperature of from 100° C. to 400° C. and at a pressure of from $1.2\times10^5$ to $51\times10^5$ Pa of a $C_4$-hydrocarbon selected from the group consisting of a saturated $C_4$-hydrocarbon, an unsaturated $C_4$-hydrocarbon and mixtures thereof, an oxygen-containing gas and water vapor and in the presence of at least one catalyst to produce a reactor outlet gas;

reducing acid concentration in a recirculated portion of said reactor outlet gas by means of separating crude acid from said reactor outlet gas by using a countercurrent scrub; and recirculating in a reaction gas circuit part of said reactor outlet gas from said countercurrent scrub.

2. The process as claimed in claim 1, comprising
using a solvent in the countercurrent scrub which is a compound selected from the group consisting of diphenyl oxide, biphenyl, aromatic ketones and ethers, aliphatic ketones and ethers, water, phthalic acid, phthalic acid derivatives, phthalide, aliphatic dicarboxylic acids, adipic acid, adipic acid derivatives, maleic acid, maleic acid derivatives, carboxyacetic acids, benzoic acid, benzoic acid derivatives, lactones, propylene carbonate, dialkyl carbonates, trialkyl phosphates, trialkylamines, sulfolane, sulfolane derivatives, alkylpyrrolidones, low molecular weight liquid polymers, low molecular weight oligomers, polyvinylates, polyacrylates, polyethers, polyketones, and mixtures thereof.

3. The process as claimed in claim 1, comprising
using water as a solvent in the countercurrent scrub.

4. The process as claimed in claim 1, comprising
carrying out the countercurrent scrub in an absorption tower containing random packing elements.

5. The process as claimed in claim 1, comprising
carrying out the countercurrent scrub in an absorption tower containing ordered packing.

6. The process as claimed in claim 1, comprising
carrying out the countercurrent scrub in an absorption tower containing internal fittings selected from the group consisting of separation trays, bubble cap trays, valve trays, sieve trays, and mesh trays.

7. The process as claimed in claim 1, comprising
carrying out the countercurrent scrub in a tower selected from the group consisting of a trickle tower and a spray tower.

8. The process as claimed in claim 1, comprising
carrying out the countercurrent scrub in an absorber containing moving internal fittings.

9. The process as claimed in claim 1, comprising
recirculating all or part of water obtained in concentrating and purifying of the crude acid to the countercurrent scrub.

10. The process as claimed in claim 1, comprising
recirculating to the countercurrent scrub all or part of low boilers obtained.

11. The process as claimed in claim 1, comprising
taking a waste gas stream from said reaction gas circuit after said countercurrent scrub.

12. The process as claimed in claim 11,
wherein a part of hydrocarbons present in said waste gas stream taken from said reaction gas circuit is separated from uncondensable constituents by cooling or compression; and recirculating said hydrocarbons as a recycle stream to an inlet of said reactor.

13. The process as claimed in claim 1, comprising
reducing residual acid concentration in a gas stream recirculated to the reactor to from 0.01% to 6% by volume by means of the countercurrent scrub.

14. The process as claimed in claim 1,
wherein a mass flow of recirculated gas is from 1 to 100 times a mass flow of fresh starting material fed in.

15. The process as claimed in claim 1,
wherein the $C_4$-hydrocarbons used are selected from the group consisting of n-butane, isobutane, isobutene, 1-butene, trans-2-butene and cis-2-butene, and mixtures thereof containing high proportions of these compounds.

16. The process as claimed in claim 1,
wherein the $C_4$-hydrocarbons used are raw material mixtures from the petrochemicals industry selected from the group consisting of "$C_4$ fraction" (predominantly butadiene and i-butene), "raffinate 1" (predominantly i-butene and n-butenes), "raffinate 2" (predominantly butanes, 1-butene and 2-butenes) and mixtures thereof.

17. The process as claimed in claim 1,
wherein the oxygen-containing gas used is pure oxygen.

18. The process as claimed in claim 1,
wherein oxygen concentration in a gas stream fed to the reactor is from 1% to 35% by volume.

19. The process as claimed in claim 1,
wherein a proportion of $C_4$-hydrocarbon at a reactor inlet is selected from the group consisting of (a) having butene present in an amount of from 1% to 10% by volume, either alone or in admixture with further $C_4$-hydrocarbons, and (b) having butane present in an amount of from 5% to 80% by volume, either alone or in admixture with further $C_4$-hydrocarbons.

20. The process as claimed in claim 1,
wherein the catalyst used is a coated catalyst comprising an inert nonporous support body and a catalytically active mixed oxide composition coating an outer surface of the support body; and said catalytically active mixed oxide composition comprising (a) at least one oxide selected from the group consisting of titanium dioxide, zirconium dioxide, tin dioxide and aluminum oxide and (b) from 0.1% to 1.5% by weight, based on the weight of component (a) and per m²/g of specific surface area of component (a), of vanadium pentoxide.

* * * * *